United States Patent
Villa et al.

(10) Patent No.: US 7,531,694 B2
(45) Date of Patent: May 12, 2009

(54) PROCESS FOR SYNTHESIS OF 4-4'-DIAMINO-DIPHENYL-SULFONE

(75) Inventors: Marco Villa, Padova (IT); Carla De Faveri, Farra Di Soligo (IT); Riccardo Zanotti, San Giorgio delle Pertiche (IT); Francesco Ciardella, Padova (IT); Fabrizio Borin, Selvazzano Dentro (IT)

(73) Assignee: Lundbeck Pharmaceuticals Italy, S.p.A., Padova (IT)

( * ) Notice: Subject to any disclaimer, the term of this patent is extended or adjusted under 35 U.S.C. 154(b) by 0 days.

(21) Appl. No.: 11/630,760

(22) PCT Filed: Jul. 7, 2004

(86) PCT No.: PCT/EP2004/051389

§ 371 (c)(1), (2), (4) Date: Feb. 7, 2008

(87) PCT Pub. No.: WO2006/002690

PCT Pub. Date: Jan. 12, 2006

(65) Prior Publication Data

US 2008/0293970 A1     Nov. 27, 2008

(51) Int. Cl.
*C07C 317/14*     (2006.01)

(52) U.S. Cl. .......................................... 568/28; 568/30

(58) Field of Classification Search ................... 568/28, 568/30
See application file for complete search history.

(56) References Cited

U.S. PATENT DOCUMENTS 2,227,400 A     12/1940     Roblin et al.

FOREIGN PATENT DOCUMENTS

| | | |
|---|---|---|
| EP | 0102476 | 3/1984 |
| FR | 829926 | 7/1938 |
| JP | 63035549 | 2/1988 |
| SU | 592822 | 2/1978 |

OTHER PUBLICATIONS

Cahuhan, P M S et al., Antiparasitic Agents: Part 5—Synthesis of 4-(Substituted-aryl)amino-7-chloroquinolines as Potential Antimalarial Agents, Indian Journal of Chemistry, Lucknow, India, vol. 25B, 1986, pp. 1142-1145.

Tercio, J. et al., "Synthesis of Dapsone and Acedapsone under Phase Transfer Conditions," Anais Da Academia Brasileira De Ciencias, 1988, pp. 431-434.

*Primary Examiner*—Sikarl A Witherspoon
(74) *Attorney, Agent, or Firm*—Ohlandt, Greeley, Ruggiero & Perle, L.L.P.

(57) ABSTRACT

A new process for the preparation and purification of 4-4'-diamino-diphenyl-sulfone (dapsone) is described. The process described is a three step process comprising a condensation reaction with the synthesis of a thioether intermediate and then steps of oxidation and reduction in suitable conditions in order to obtain a product with good yield and purity.

9 Claims, No Drawings

PROCESS FOR SYNTHESIS OF 4-4'-DIAMINO-DIPHENYL-SULFONE

FIELD OF THE INVENTION

The present invention relates to a process for the preparation of 4-4'-diamino-diphenyl-sulfone.

PRIOR ART 4-4'-diamino-diphenyl-sulfone also known as dapsone (DDS) is a widely employed chemical entity, being used both as hardening agent in the curing of epoxy resins and as a therapeutic agent for treatment of bacterial infections in humans and animals, approved as an antibiotic by the Food and Drug Administration since 1963. As for its use in human medicine, dapsone is, in fact, an effective antibiotic used at the beginning for treatment of leprosy and later on as suppressant of dermatitis herpetiformis. More recently dapsone has been used as effective antibiotic for prophylaxis against *pneumocystis carinii* pneumonia (PCP), an opportunistic disease in HIV infection, often diagnosed when the pathology is severe, occurring very frequently in women where it seems to be the first or the second AIDS-related illness. Therefore the therapeutic interest in this antibacterial agent has been renewed and increased.

One of the first synthesis description for DDS is reported in 1938 in FR829926 among those of other diamino-diphenyl-sulfone colorant intermediates. The product was obtained at that time heating the 4,4'-dichloro-diphenyl-sulfone with 25% ammonia.

More recent DDS synthesis processes described are based essentially on reactions of condensation of para substitued-phenyl compounds and/or oxidation of para substituted-diphenylsulfides compounds and eventually reduction. A process where all these reactions are combined is also described.

SU302338 describes a single step synthesis of DDS avoiding the step of condensation. The product is obtained oxidising the starting material AcNH-phenyl —S— phenyl-NHAc with $H_2O_2$ at temperatures of 20-40° C. at acid pH for $H_2SO_4$ and then hydrolysing with the same acid heating up to 80-100° C.

SU592822 improved the synthesis process of SU193497 always avoiding the step of condensation, but oxidising the starting material 4,4'nitro-diphenyl-sulfide with diluted nitric acid in presence of $FeCl_3$ and then reducing with Fe in alkalinised aqueous medium with ammonium chloride at 70-82° C.

In JP63035549 the product is obtained in mixture with 4-bromo,4'-amino-diphenyl-sulfone by treating starting material 4,4'-dibromo-diphenyl-sulfone with ammonia at 30-132.4° C. in presence of a catalyst consisting of Cu or a Cu compound.

In all the cases above mentioned the starting material was a parasubstitued-diphenyl-sulfides or parasubstitued-diphenyl-sulfone.

In EP 0102476 a method for synthesis of 4,4'-diamino-diphenyl-sulfone is further disclosed, the process being performed: a) condensing 4-aminothio-phenol and 4-chlorobenzene, b) oxidising the thioether obtained by using an oxidation system formed by 30% aqueous hydrogen peroxide in glacial acetic acid at 100° C. and then c) reducing the 4-nitro,4'-amino-diphenyl-sulfone by hydrogenation in presence of a Raney-Nickel catalyst.

In a more recent one, Chauhan P. M. S. et al. (Indian Chem. J. 25, 1142-1145, 1986) describes a synthesis of DDS departing from para substituted-phenyl compounds, where a para-substitued-diphenyl-sulfide is an intermediate. The DDS synthesis, in fact, is obtained by condensing 4-chloronitrobenzene and 4-chloroacetanilide in presence of sodium sulfide and obtaining the parasubstitued-diphenyl-sulfide intermediate subsequently oxidised $KMnO_4$. The oxidised intermediate obtained is deacetylated and reduced for hydrogenation in presence of Raney-Nickel catalyst, a known catalyst for this type of reaction. Either purity of the product or yield of the process are not mentioned.

Long before Chauhan P. M. S. et al., other processes for parasubstitued-diphenyl-sulfide and parasubstituted-diphenyl-sulfone intermediates have been described.

U.S. Pat. No. 2,227,400 describes the process for synthesis of acylamino-nitro-diphenyl-sulfones by reacting p-acylamino-benzene sulfinic acid with p-nitrochloro (or bromo)-benzene in solvents having boiling point from 150° C. to 180° C., and preferably cyclohexanol, in presence of potassium acetate with a yield of 50%, while U.S. Pat. No. 2,385,899 describes the process for synthesis of diphenyl sulfones by oxidising with sodium hypochlorites 4,4'-di(acetylamino) diphenyl-sulfides in acetic acid solution at 85° C.

SUMMARY

For the purpose to implement an industrial process efficient, cost effective and with good yield and purity of the final product for the synthesis of 4-4'-diamino-diphenyl-sulfone, particular attention has to be given to the starting materials and reagents as well as to the reaction conditions of the all steps of synthesis, being the reactions of condensation of para substituted-phenyl compounds or oxidation of para substituted-diphenylsulfide compounds and eventually reduction of unavoidable steps.

At this purpose the Applicant has developed a new process for the synthesis of 4-4'-diamino-diphenyl-sulfone, resulting from a combination of the essential reactions of condensation, oxidation and reduction but taking in consideration the industrial need to operate in mild conditions and with easy available and easy to handle reagents. This synthesis process has been surprisingly found more favourable either for purity and yield of the final product, while costing advantageous and easily available starting products and reagents are used.

Therefore, it is an object of the present invention a process for the synthesis of 4-4'-diamino-diphenyl-sulfone characterised by the following steps:

condensation reaction from 4-aminothio-phenol and 4-chloro-nitrobenzene with formation of 4-(4'-nitrophenylsulfanyl)-phenylamine at temperatures from 45° C. to reflux temperatures of the reaction mixture;

oxidation of the thioether formed in the previous step with an oxidising system formed by $Na_2WO_4$ and $H_2O_2$ into the corresponding sulfone, wherein the $Na_2WO_4$ is added in an aqueous solution at 0.1-3% molar concentration and then a solution of 35% hydrogen peroxide 1.0-1.3 eq. at temperatures from 50° C. to 85° C. is slowly added;

reduction of 4-nitro, 4'-aminoacetyl-diphenyl-sulfone by hydrogenation in presence of a Pd/C or Pt/C catalyst obtaining the 4-4'-diamino-diphenyl-sulfone.

DETAILED DESCRIPTION OF THE INVENTION

The aims and advantages of the process for the synthesis of 4-4'-diamino-diphenyl-sulfone object of the present invention, will be better understood in the course of the following detailed description.

It is well known that in the DDS synthesis processes a number of by-products are obtained (Sengupta C et al. Indian J. Pharm. Sci. 44, 14-15, 1982). The limiting step in a DDS synthesis process, industrially effective for purity and yield, is related to the achievement of the para substituted-diphenylsulfones in high yield in term of quantity and quality, and at this purpose the condensation and even more the oxidation steps are critical.

In Chauhan P. M. S. et al. (1986, ref. cit.) the starting materials for DDS synthesis are 4-chloronitrobenzene and 4-chloroacetanilide and sodium sulfide and the oxidising agent consists of a potent oxidising agent such as $KMnO_4$.

Also in U.S. Pat. No. 2,227,400 is described the process for synthesis of acylamino-nitro-diphenyl-sulfone intermediate but the reaction is carried out with not easy accessible starting materials in solvents having an high boiling point from 150° C. to 180° C., and preferably cyclohexanol (b.p. 160-161° C.), with a very poor yield of 50% (maximum yield obtained). This reaction is therefore disadvantageous for an industrial process either for reaction conditions (i.e. high temperatures employed) and yield.

The synthesis process of 4-4'-diamino-diphenyl-sulfone, object of the present invention, starts from available and cheap raw materials (4-mercaptoaniline and 4-chloronitrobenzene) from which the sulphide intermediate is easily obtained and employs as oxidising a system $H_2O_2/Na_2WO_4$ unexpectedly more advantageous than permanganate. This synthesis process allows the preparation of the final product according to the following scheme:

1° step: condensation of 4-mercaptoaniline and 4-chloronitrobenzene obtaining 4-(4'-nitrophenylsulfanyl)-phenylamine;

2° step: oxidation of 4-amino, 4'nitro-diphenyl-sulfide obtaining 4-amino, 4'nitro-diphenyl-sulfone;

3° step: reduction of 4-amino, 4'nitro-diphenyl-sulfone obtaining 4,4'di amino-diphenyl-sulfone.

Two further reactions of protection and deprotection of the amino group of the intermediates before and after oxidation at the step 2 are preferentially implemented.

First Step

This step can be carried out under very different conditions since the reactivity of both the reagents is quite relevant, being the substrate reactive toward the oxygen. Therefore the reaction has to be preferentially performed under phase transfer conditions in organic solvents and water and inert atmosphere.

The reaction is carried out by adding 4-mercapto aniline (fused or as a solution in an organic solvent) in a mixture of 4-chloronitrobenzene (1.0-1.3 eq. preferably 1.05), organic solvent and (15%) of an alkali (1.05-1.15 eq. preferably 1.10) in water preferentially in presence of phase transfer catalyst such as tetrabutyl ammonium hydrogensulphate (5% molar) at a temperature between 60° C. to reflux. To better control the reaction heat, the substrate is preferentially added in about two hours at 45° C. to reflux of reaction mixture preferably at 80-85° C. After separation of the phases and washings of the organic phase with diluted aqueous acid solution the product can be directly crystallised from the organic solvent employed.

Organic solvents useful for this reaction can be organic solvents selected in the group formed by toluene, methyl tert-butylether (MTBE), xylenes, chlorobenzene, dimethylformamide (DMF), dimethyl-sulphoxide (DMSO), being toluene or mixtures of these organic solvents with toluene the preferred ones.

Different inorganic bases such as sodium hydroxide, sodium or potassium carbonate, potassium hydroxide are suitable without affecting reaction yield.

This step proved to be very convenient since proceeding under mild conditions easily feasible in an industrial process; furthermore after work up the solvent is suitable for crystallisation giving the product in high yields and quality.

If the reaction is contaminated by the product arising from the oxidative dimerization of the thiol group, this by-product can be removed through an extraction in acidic condition with diluted $H_2SO_4$ (i.e.) without affecting the yield of the product.

The product directly crystallised from organic solvents is obtained in a very high yield (91–95%) with a purity >99% determined via HPLC.

Second Step

The oxidation step can be carried out directly, without protection, on 4-(4-nitrophenylsulfanyl)-phenylamine under acid conditions employing an environmental clean and mild oxidant such as hydrogen peroxide in combination with sodium tungstate as catalyst, but in order to obtain good yield and purity of the final product, as for the purposes of the process, a protection of the amino group of the intermediate obtain in the previous step is preferentially carried out.

The whole sequence (protection-oxidation-deprotection) is preferentially carried out without isolation of the intermediate.

Protection is realised by adding acetic anhydride or any suitable protecting group suitable for amino groups known by a person skilled in the art (see Green T. W., Protective Groups in Organic Synthesis $3^{rd}$ Edition, Wiley Interscience) to the substrate in acetic acid at the temperature between 25° and 80° C., preferably 50°-60° C. The reaction is complete and quantitative in about 30 min. from the end of the addition.

At the end the mixture is added with $Na_2WO_4$ (0.1-3%, preferably 1% molar) previously dissolved in the suitable amount of water, usually 4-5 preferably 4 times of the weight ratio. Then a solution of commercial and stable 35% hydrogen peroxide 1.0-1.3 eq. preferably 1.05 eq. is slowly added at temperatures from 50° to 85° C. in 1-5 hours.

At reaction completion (2-3 hours) the product can be isolated by water addition, cooling down to room temperature and filtering to yield the acetyl derivative that can be hydrolysed separately.

More conveniently, the solvent can distilled or suck away of and the residue added with 21% HCl in water (up to 8 liter/kg of substrate). The mixture is heated to reflux while part of the solvent is distilled off concentrating the mixture to 3-5 volumes with respect to the substrate. At the end the reaction can be diluted with water and the product isolated by filtration at room temperature.

By products finally present can be removed by treatment with mixture of toluene and acetone at 50° C.; after cooling the clean product is recovered by filtration.

Third Step

Final reduction is conveniently carried out with Pd/C 0.5%, preferably, or Pt/C as catalyst in a mixture of methanol and water preferentially in presence between 0 and 2 eq., preferably between 1 to 2, of an acid (such as for example methansulfonic acid) at 50-60° C. Alternative acid to methansulfonic are represented by HCl, p-Toluenesulphonic acid, HBr, trifluoroacetic acid, and sulfuric acid with HCl and PTSH as preferred choices after methansulfonic acid. The amount of the acid can vary between 0 to 2 eq., preferably between 1 to 2.

The hydrogenation is carried out in 1 to 4 hours, usually faster than in conventional descriptions and is quantitative and proceeds at moderate pressure (14 bar).

After standard work up the product is precipitated after distillation of the solvent and neutralization with ammonium hydroxide.

Final purification from organic solvents gives a product with high purity and yield to obtain a product suitable for pharmaceutical application. The solvents for this step can be methanol, ethanol, isopropanol, ethylene glycol, ethyl acetate, methyl tert-butyl ether, methanol, isopropanol, MTBE with alcoholic solvents and their mixture with water are preferred choices.

The known catalyst for this reaction, nickel, produces a worse result.

The following examples are given for illustrative and not limiting purpose of the present invention.

EXAMPLE 1

Preparation of
4-(4'-nitro-phenylsulfanyl)-phenylamine

A solution of 4-amino-benzenethiol (1.00 Kg, 7.99 mole) is dissolved under nitrogen in toluene (2 lt) and slowly added under mechanical stirring to a reactor containing a mixture of 4-1-chloro-4-nitro-benzene (1.32 Kg; 8.38 mole), toluene (2 lt), 30% sodium hydroxide (1.17 Kg; 8.78 mole) and tetrabutyl-ammonium hydrogensulphate (68 g; 0.2 mole). During the addition the reaction temperature is maintained at about 85° C.; the mixture is then kept at the same temperature for about two hours. The mixture is added with toluene and the phases are separated at about 85° C. The organic phase is then washed with diluted sulphuric acid, the organic phase is concentrated under vacuum to about 4 liters and cooled. The crystallized product is then isolated by filtration, washed and dried under vacuum at 60° C. 1.87 Kg of pure 4-(4-Nitro-phenylsulfanyl)-phenylamine are obtained (95% yield; 99% purity).

EXAMPLE 2

Preparation of
N-[4-(4-Nitro-benzenesulfanyl)-phenyl]-acetamide

A reactor flask, maintained under nitrogen, is charged with acetic acid (4 lt) and 4,(4'-nitrophenylsulfanyl)-phenylamine (1 kg; 4.06 mole) The mixture is heated to 50-55° C., and added in one hour with acid anhydride (0.46 Kg; 4.47 mole). The acetic acid (3 lt) is charged and the mixture heated under vigorous mechanical stirring to 85° C. Charge first a solution of sodium tungstate dihydrate (13.4 g; 0.041 mole) in water (50 ml) and immediately after, while maintaining the temperature at about 85° C., in about two hours, a solution of 35% hydrogen peroxide (0.83 Kg; 8.53 mole) At the end of the addition, the mixture is kept at 85° C. for two hours. Concentrate the reaction mixture by distilling the solvent under vacuum at 70-80° C. to obtain a residue (to about 2 Kg).

Charge under stirring 21% HCl (10 lt.) and heat the mixture under stirring to reflux. After one hour, begins the distillation at atmospheric pressure of about 7 liters of solvent (95% yield; 97.% purity).

EXAMPLE 3

Preparation of
N-[4-(4-Nitro-benzenesulfonyl)phenyl]acetamide

A 250 ml three-necked round bottom flask is charged with methanol (70 ml) N-[4-(4'-Nitro-benzenesulfanyl)-phenyl] acetamide (10 g), oxalic acid (5.1 g) and sodium tungstate dihydrate (0.26 g). the mixture is heated to 50° C. and hydrogen peroxide 35% (9 ml) is added. At the end of the addition the mixture is kept at 50-55° C. for five hours. The mixture is treated with 30% ammonia (10 ml) and diluted with water (140 ml), the cooled. The product is isolated at room temperature by filtration (83% yield; >90% purity by TLC).

EXAMPLE 4

Preparation of
N-[4-(4-Nitro-benzenesulfonyl)-phenyl]-acetamide

A reactor flask is charge with N-[4-(4'-Nitro-benzenesulfanyl)-phenyl]-acetamide (150 g), methanol (1500 ml) and methansulfonic acid (55 g). The suspension is heated up to 57° C. and then sodium tungstate dihydrate (2 g) is added. Hydrogen peroxide 10% (676 g) is added drop-wise over two hours. The reaction is kept in the range 55-60° C. for three hours. The mixture is neutralised by ammonia and after cooling down to room temperature the product is isolated by filtration. 154 g of (4-nitro-phenylsulfanyl)-phenylamine are obtained (90% yield; >90% purity by TLC).

EXAMPLE 5

Preparation of Dapsone

Charge an hydrogenation vessel with 4-(4'-nitro-benzenesulfonyl)-phenylmanine (380 g; 1.36 mole), water (220 ml), methanol (910 ml) and methansulfonic acid (187-kg; 1.95 mole). Then charge under nitrogen, 5% palladium on charcoal (14.4 g; 0.0067 mole). After inertization, the mixture is added with hydrogen under vigorous stirring up to 4 bar and then heated to 50° C. The mixture is maintained under the above conditions for the least 4 hours. After reaction completion the reactor is purged with nitrogen several times and the catalyst filtered off. The filter is washed with methanol (25 ml) and water (200 ml) and the solution is concentrated under vacuum below 50° C. to remove the organic solvent. At the end, then the mixture is neutralised with 15% ammonia at 50° C., then cooled and the product isolated by filtration.

After drying, 315 g of crude product is obtained. Product is crystallised from isopropanol (1000 ml) and water (700 ml) to give 302 g of pure product (80% yield; >90% purity).

EXAMPLE 6

Preparation of Dapsone

In a hydrogenation vessel 4-(4'-Nitro-benzenesulfonyl)-phenylamine (100 g), p-toluensulfonic acid (68.4 g), methanol (350 ml), water (150 ml) and 10% palladium on charcoal (7.6 g) are charge. The mixture is allowed to react with hydrogen at approximately 50° C. and 5 bar pressure. At reaction completion, hydrochloric acid is added, the catalyst is filtered and dried. 82 g of crude Dapsone are obtained (82% yield; >99.5% purity).

| Physico-chemical characterization of Dapsone | |
|---|---|
| Melting point | 175-181° C. |
| $^1$HNMR (DMSO-d$_6$) | δ (300 MHz): 5.9(4H; bs; 4,4'-NH$_2$), 6.4(4H; d; J = 9Hz; 3,5 and 3',5'-H), 7.5(4H; d; J = 9Hz; 2,6 and 2',6'-H) |
| $^{13}$CNMR (DMSO-d$_6$) | δ (75 MHz): 113.70(3,5 and 3',5'-C), 128.99(4,4'-C), 129.41(2,6 and 2',6'-C), 153.59(6-C) |
| IR (v/cm$^{-1}$) | From 3336 to 3454 stretching —NH2 1630-1590 bending-NH2 1338-1446-1106 Bending-SO2 <900 C—H Finger print for aromatic protons |
| MS (m/z) | 248 (M$^{+\cdot}$) |

Further on the disadvantages before mentioned, it is also known that the synthesis processes for dapsone are limited by low yields and production of a number of by-products, forming in some extent a remarkable industrial waste. At the purpose to recover these by-products a complex method to convert these by-products is described (Sengupta, C. et al. 1982, ref. cit.), but this method is very difficult to implement in an industrial process due to the need of many separations, purifications and conversion reactions in dapsone.

On the contrary, the process for synthesis of 44'-diamino-diphenyl-sulfone described in the present application has many advantages for the industrial application. In fact all the three steps are performed at mild temperatures and in any cases below 100° C. in organic solvents commonly used in organic chemistry and cheap and easy available reagents. Furthermore the quantitative and qualitative yields of everyone of the steps are remarkable and the purifications are easily feasible in an industrial plant, being at the end of the first and second step limited to an extraction, and crystallisation from solvent reaction medium and washings with solvents respectively.

The results herein described demonstrate that the process according to the present invention permit an efficient and cost effective synthesis of 4-4'-diamino-diphenyl-sulfone, thus fulfilling the purposes of the present invention.

The invention claimed is:

1. A process for synthesis of 4-4'-diamino-diphenyl-sulfone characterised by the following steps:
    condensation reaction of 4-aminothio-phenol and 4-chloro-nitrobenzene with formation of 4-nitro-4'-amino-diphenyl-sulfide at temperatures from 45° C. to reflux temperatures of the reaction mixture;
    oxidation of the thioether with an oxidising system comprising Na$_2$WO$_4$ and H$_2$O$_2$ into the corresponding sulfone, wherein the Na$_2$WO$_4$ is added in an aqueous solution at 0.1-3% molar and then a solution of 35% hydrogen peroxide 1.0-1.3 eq. at temperatures from 50° C. to 85° C. is slowly added;
    reduction of the 4-nitro-4'-amino-diphenyl-sulfone by hydrogenation in the presence of a Pd/C or Pt/C catalyst obtaining the 4-4'-diamino-diphenyl-sulfone.

2. The process for synthesis of 4-4'-diamino-diphenyl-sulfone according to claim 1 wherein a reaction of protection and a reaction of de-protection are performed before and after oxidation of step 2 on the amino group of the intermediates obtained in steps 1 and 2.

3. The process for synthesis of 4-4'-diamino-diphenyl-sulfone according to claim 1 wherein the condensation reaction is performed in organic solvents selected from the group consisting of toluene, methyl tert-butylether xylenes, chlorobenzene, dimethylformamide, and dimethyl-sulphoxide.

4. The process for synthesis of 4-4'-diamino-diphenyl-sulfone according to claim 3 wherein the organic solvents are selected from the group consisting of toluene or mixtures thereof with methyl tert-butylether, xylenes, chlorobenzene, dimethylformamide, and dimethyl-sulphoxide.

5. The process for synthesis of 4-4'-diamino-diphenyl-sulfone according to claim 1 wherein the temperatures of step 1 are from 80 to 85° C.

6. The process for synthesis of 4-4'-diamino-diphenyl-sulfone according to claim 1 wherein the condensation reaction is performed in the presence of a phase transfer catalyst.

7. The process for synthesis of 4-4'-diamino-diphenyl-sulfone according to claim 1 wherein the oxidation reaction is performed in acidic conditions adding Na$_2$WO$_4$ at 1% molar and then a solution of 35% hydrogen peroxide 1.05 eq. is added in 1-5 hours.

8. The process for synthesis of 4-4'-diamino-diphenyl-sulfone according to claim 1 wherein the hydrogenation is performed in 1 to 4 hours at 50-60° C. in the presence of 0.5% Pd/C catalyst in a mixture of methanol and water.

9. The process for synthesis of 4-4'-diamino-diphenyl-sulfone according to claim 8 wherein the hydrogenation is performed in the presence of 1 or 2 eq. of an acid selected from the group consisting of methansulfonic acid, HCl, p-toluenesulphonic acid, HBr, trifluoroacetic acid and mixture of sulfuric acid with HCl and p-toluenesulphonic acid.

* * * * *